United States Patent [19]
Hutchins et al.

[11] Patent Number: 5,415,489
[45] Date of Patent: May 16, 1995

[54] RECIPROCATING DRIVER APPARATUS

[75] Inventors: Burleigh M. Hutchins, Milford; Raymond R. Dunlap, Douglas; Timothy J. Conklin, Lynnfield; Bruce A. Swanson, Mansfield; John Petracca, W. Upton; Louis Abhrahams, Worcester; Ronald A. Kimball, Brookfield, all of Mass.

[73] Assignee: Zymark Corporation, Hopkinton, Mass.

[21] Appl. No.: 154,048

[22] Filed: Nov. 17, 1993

Related U.S. Application Data

[62] Division of Ser. No. 2,156, Jan. 11, 1993, abandoned.

[51] Int. Cl.⁶ ............................................. F16C 11/08
[52] U.S. Cl. ..................................... 403/76; 403/122; 403/180; 403/287; 74/89.15
[58] Field of Search ............... 403/122, 59, 63, 24, 403/26, 60, 52–53, 76, 121, 287, 180, 182–184; 74/89.15; 92/129; 210/101, 198.2

[56] References Cited

U.S. PATENT DOCUMENTS

| 3,008,340 | 11/1901 | Chillson | 74/89.15 |
| 3,049,800 | 8/1962 | Neff et al. | 403/122 X |
| 3,110,510 | 11/1963 | Berner | 403/59 |
| 4,639,245 | 1/1987 | Pastrone et al. | 74/89.15 X |
| 4,790,236 | 12/1988 | MacDonald et al. | 92/129 |
| 5,100,305 | 3/1992 | Zirps | 92/129 X |

Primary Examiner—Randolph A. Reese
Assistant Examiner—Harry C. Kim
Attorney, Agent, or Firm—John E. Toupal; Harold G. Jarcho

[57] ABSTRACT

A mechanical coupling including a drive shaft reciprocable on an axis; an actuator shaft mounted for reciprocating rectilinear motion on the axis; and a coupling mechanism for transmitting reciprocating motion of the drive shaft to the actuator shaft; the coupling mechanism including a pivot joint allowing relative pivotal movement between the drive shaft and the actuator shaft, and a translational joint allowing relative translational movement between the drive shaft and the actuator shaft in directions transverse to the axis, the translational joint having a flexible link connecting the pivot joint and the drive shaft.

20 Claims, 12 Drawing Sheets

RECIPROCATING DRIVER APPARATUS

This is a divisonal of application Ser. No. 08/002,156, filed on Jan. 11, 1993, now abandoned.

BACKGROUND OF THE INVENTION

This invention relates generally to liquid chromatography apparatus and, more particularly, to a liquid chromatography pumping system that delivers fluids at precisely metered rates.

Prior fluid pumps used in high pressure liquid chromatography systems have been designed with one or two pistons utilizing spring or gravity loaded ball and seat check valves of very hard material. Each pressuring chamber of such pumps is normally equipped with two such check valves, one on the inlet side and one on the outlet side of the chamber. Typically, the piston of the pump runs in a high pressure sealing system that wears and will leak after some time in service. In addition, prior pumps have been very sensitive to dissolved gas contained in the liquids being pumped. Gas liberated due to reduced pressures during the inlet phase of operation can accumulate in the pumping chamber and will not be expelled through the outlet because of the back pressure present. Consequently, the pump will stop pumping liquid. Other problems are produced by typical hard seat check valves which can be propped open by particulate matter and leak. Also, ordinary inlet valves are opened on an inlet stroke by suction that contributes to undesirable gas generation from the liquid being pumped.

Other problems associated with liquid chromatography systems stem from the fixed mechanical mechanisms used to connect plungers and driving mechanisms in ordinary pumps. The alignment in such pumps is never perfect and results in wear of the plunger and seal material resulting in shortened intervals between replacement of these parts. In addition, pumping losses in prior systems generate heat that increases the temperature of the liquid being pumped and in many applications the increased temperature interferes with required measurements.

In most prior systems, dual piston pumps have been used to minimize pressure pulsation in the liquid flow. However, the two pistons are driven by a single motor or other driving mechanism and undesirable interactions occur when the delivery of liquid is switched from one piston to the other. Many schemes have been developed to vary the speed of the driver to compensate for these interactions, but they can never be eliminated as long as the two pistons are linked.

The object of this invention, therefore, is to provide an improved pumping system that alleviates the problems associated with prior liquid chromatography systems.

SUMMARY OF THE INVENTION

The invention is a machine including a drive shaft adapted for reciprocating motion on an axis; an actuator shaft mounted for reciprocating rectilinear motion on the axis; and a coupling mechanism coupling one end of the drive shaft to one end of the actuator shaft so as to transmit therebetween the reciprocating motion; the coupling mechanism including a pivot joint for allowing relative pivotal movement between the drive shaft and the actuator shaft, and a translational joint for allowing relative translational movement between the one end of the drive shaft and the one end of the actuator shaft in directions transverse to the axis. By allowing both pivotal and translational motion, the coupling accommodates axial misalignment between the drive and actuator shafts.

According to one feature of the above invention, the pivot joint is fixed to the one end of the actuator shaft, and the translational joint is connected to the one end of the drive shaft. Effective coupling operation is provided by this structural arrangement.

According to other features of the above invention, the pivot joint is a ball and socket joint, and the translational joint comprises an annular ball bearing assembly disposed concentrically with the axis and engaged between a planar surface portion of the socket and a planar surface on the one end of the drive shaft. Desired operation is facilitated by these joint arrangements.

According to a further feature of the invention, the translational joint further comprises a flexible connector connecting the ball and socket joint and the one end of the drive shaft. The flexible connector simplifies assembly of the coupling.

According to an additional feature of the above invention, the coupling further comprises a fastener allowing separation of the drive shaft and the actuator shaft in response solely to the application therebetween of opposing forces aligned with the axis. The fastener simplifies coupling and decoupling of drive and actuator shafts.

DESCRIPTION OF THE DRAWINGS

These and other objects and features of the invention will become more apparent upon a perusal of the following description taken in conjunction with the accompanying drawings wherein.

DESCRIPTION OF THE PREFERRED EMBODIMENT

Figure 1:
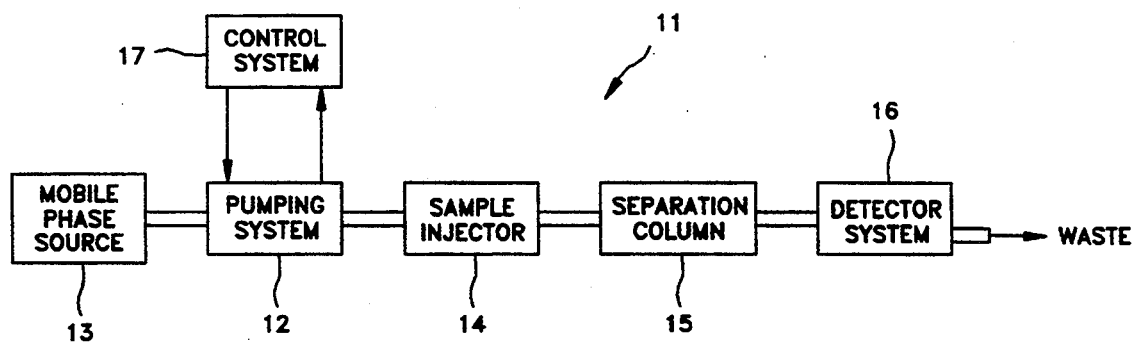
FIG. 1 is a block diagram of a liquid chromatography system according to the present invention.

A liquid chromatography apparatus 11 includes a pumping system 12 that receives liquid solvent from a mobile phase source 13. After injection of a sample by a sample injector 14, the mobile phase from the source 13 is pumped by the pumping system 12 into a separation column 15. A detector system 16 analyzes the output of the separation column 15 to determine characteristics of the injected samples. Operation of the pumping system 12 is controlled by a computer control system 17.

Figure 3:
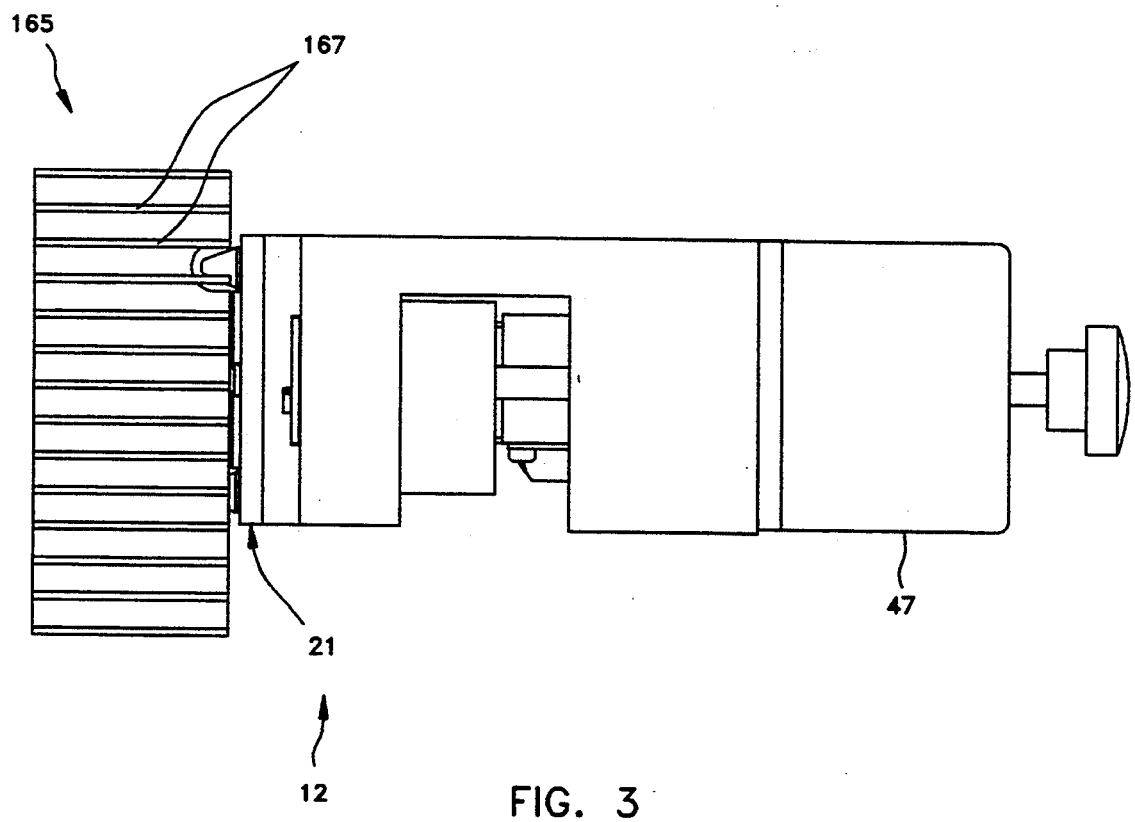
FIG. 3 is a top view of the pumping system shown in FIG. 2.
Figure 4:
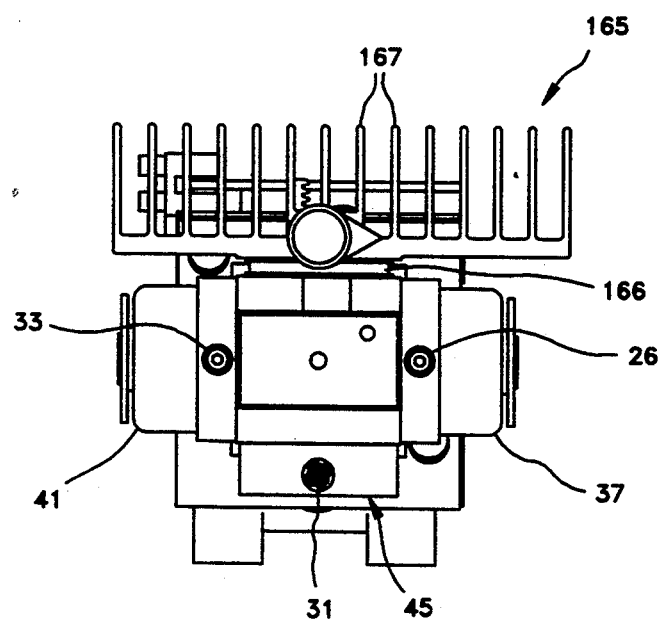
FIG. 4 is an end view of the pumping system shown in FIG. 2.
Figure 5:
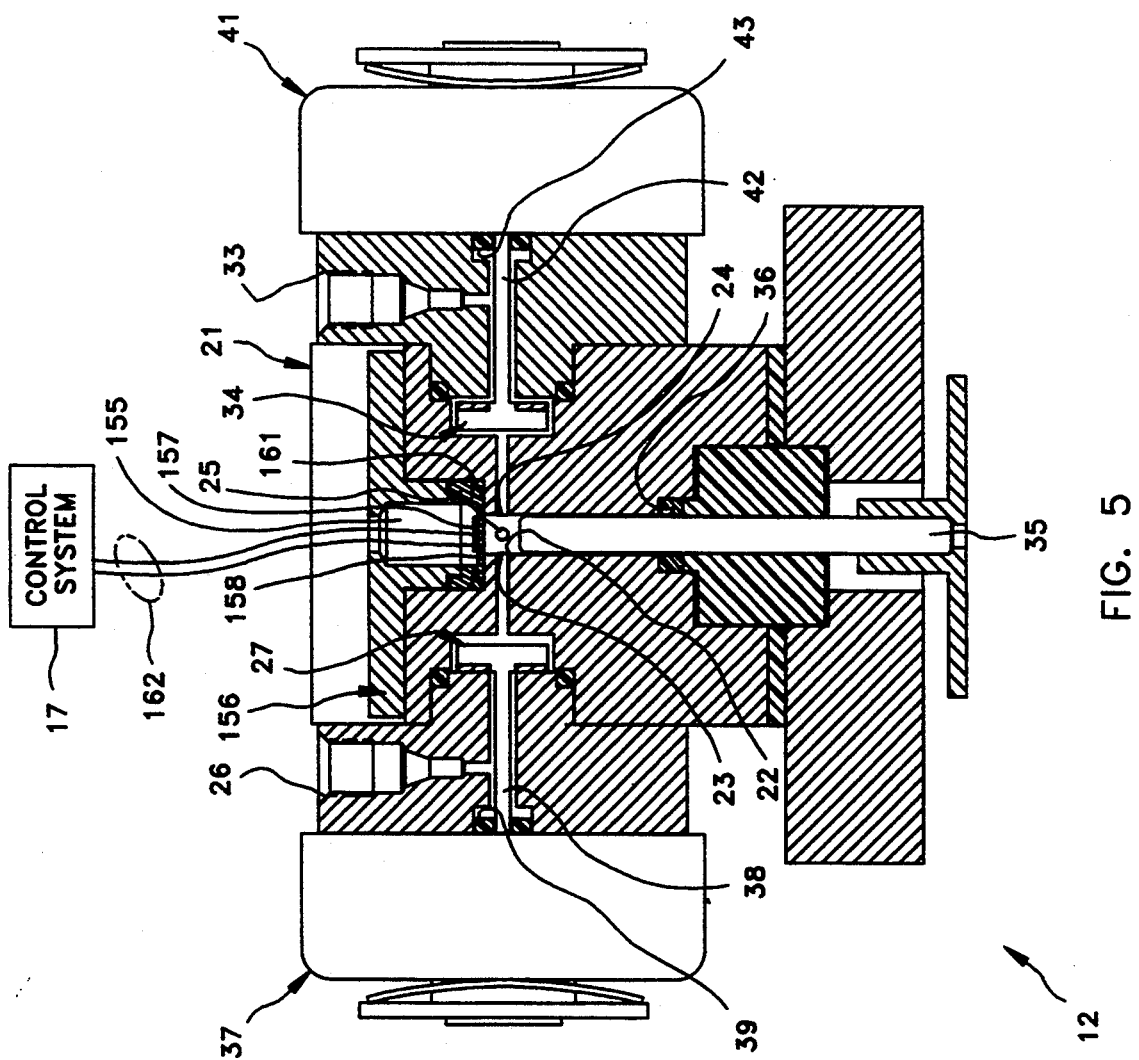
FIG. 5 is a partially cut away top view of the pumping system shown in FIGS. 2–4.

As shown in FIGS. 2–5, the pumping system 12 includes a pump head assembly 21 which defines a cylindrical pump chamber 22 having an inlet port 23, a purge port 24 and an outlet port 25 (FIG. 5). Also defined by the head assembly 21 and shown in FIG. 5 are an inlet opening 26 that is connected to the mobile phase source 13 and communicates with the inlet port 23 via an inlet valve 27; and a purge opening 33 at atmospheric pressure and communicating with the purge port 24 via a purge valve 34; and an outlet opening 31 (FIG. 5a) connected to the separation column 15 and communicating with the outlet port 25 via an outlet valve 32. A plunger piston 35 is mounted for reciprocating movement within the pump chamber 22 and is liquid sealed therein by an annular seal 36. Retained by the head assembly 21 is an inlet solenoid 37 having an inlet actuator 38 (FIG. 5) coupled to the inlet valve 27 and liquid sealed by an annular seal 39. Similarly retained by the pump head 21 is a purge solenoid 41 having a purge actuator 42 coupled to the purge valve 34 and liquid sealed by an annular seal 43. The inlet solenoid 37 and the purge solenoid 41 receive operating signals from the control system 17 shown in FIG. 1.

Figure 6:
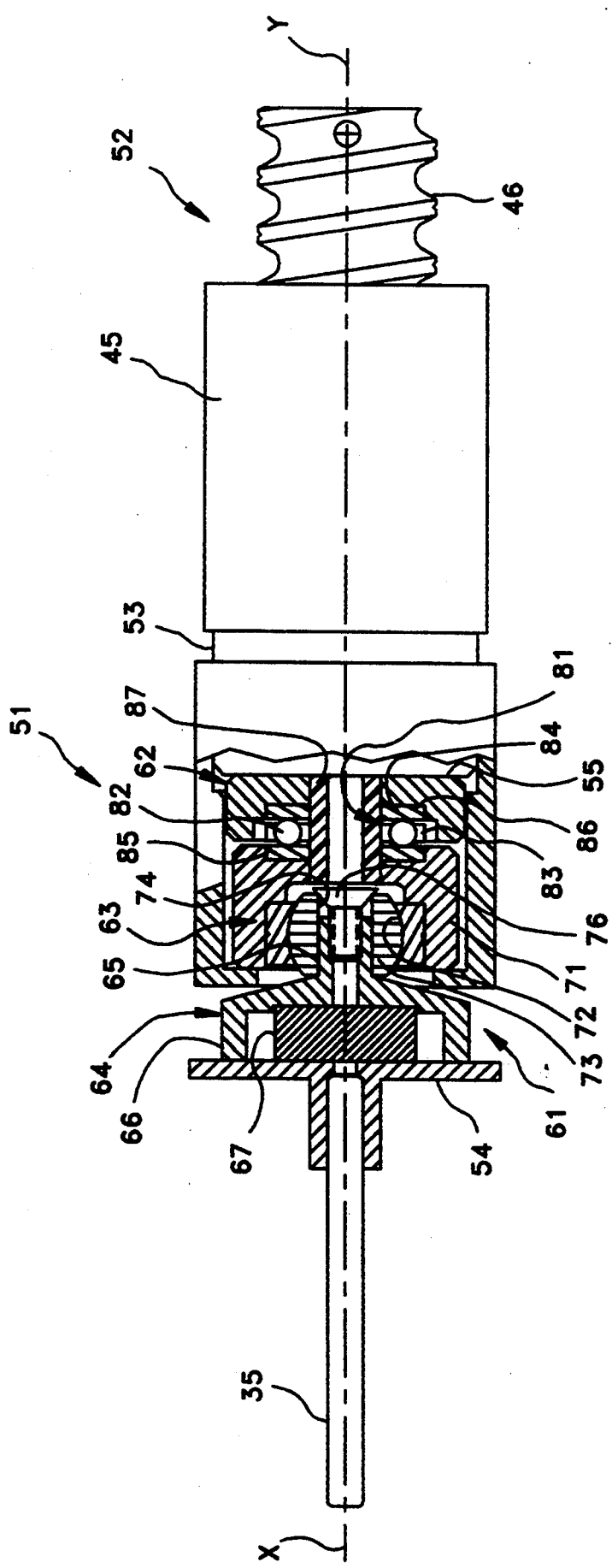
FIG. 6 is a cross sectional view of a drive coupling assembly used in the pumping system of FIGS. 2–5.

A coupling assembly 51 (FIG. 6) is connected between a drive mechanism 52 and the plunger 35. The drive mechanism includes a recirculating nut 45 that reciprocates on a ball screw 46 driven by a motor 47 shown in FIG. 2. Attached to the nut 45 is a drive shaft portion 53 of the drive mechanism 52. Reciprocating motion of the drive shaft 53 is transmitted to the plunger 35 by the coupling assembly 51 which is connected between a plate 54 forming one end of the plunger 35 and one end 55 of the drive shaft 53. Included in the coupling assembly 51 is a fastener 61 for attachment to the plate 54 of the actuator plunger 35, a translational joint 62 connected to the one end 55 of the drive shaft 53 and a pivot joint 63 connected between the fastener 61 and the translational joint 62. The fastener 61 includes a receptacle 64 having a stem portion 65, a cup portion 66 and a permanent magnet 67 retained thereby. Magnetic flux produced by the permanent magnet 67 and passing through the magnetic end plate 54 secures the plunger 35 to the coupling assembly 51. However, when separation of the drive mechanism 52 from the pump head 21 is desired, the coupling assembly 51 is easily detached from the end plate 54 by merely applying opposing manual forces therebetween in the direction of the plunger axis X. It should be noted that the attachment force required of the fastener 61 is small in that withdrawal strokes of the plunger 35 require relatively low force while during high pressure pumping strokes, the fastener 61 merely functions as a pusher.

The pivot joint 63 includes a cup member 71 retaining a socket insert 72 and a ball 73 rotatably supported thereby. Received by a central opening 74 in the ball 73 is the stem portion 65 which is secured therein by a screw 76. Because of the pivot joint 63 provided by the ball and socket 72, 73, the actuator shaft 35 can experience pivotal movement with respect to the drive shaft 53.

The translational joint 62 includes a ball bearing assembly 81 formed by a plurality of ball bearings 82 circumferentially spaced apart by an annular retainer 83. Receiving the ball bearing assembly 81 is a recess 84 in the one end 55 of the drive shaft 53. Engaged on opposite sides of the bearing assembly 81 are a pair of hardened flat washers 85, 86 retained, respectively, by a recess in the cup member 71 and a counterbore of the recess 84. A flexible rubber tube member 87 extends through central openings in the bearing assembly 81 and the washers 85, 86 and frictionally engages central openings in the cup member 71 and one end 55 of the drive shaft 53. Low friction contact between the ball bearings 82 and the flat washers 85, 86 permits translational movement of the one end 54 of the plunger 35 relative to the drive shaft 53 in directions transverse to the axes X, Y. The small degree of translational movement required by the translational joint 62 is not impeded by the flexible rubber tube member 87 which, however, facilitates assembly of the pivot joint 63 and translational joint 62. Because of the relative pivotal movement allowed by the pivot joint 63 and translational movement allowed by the translational joint 62, small misalignments between the plunger shaft 35 and the drive shaft 53 will not produce significant transverse loading between the plunger shaft 35 and the annular seal 36 (FIG. 5) to thereby prolong the operating life thereof.

Figure 5A:
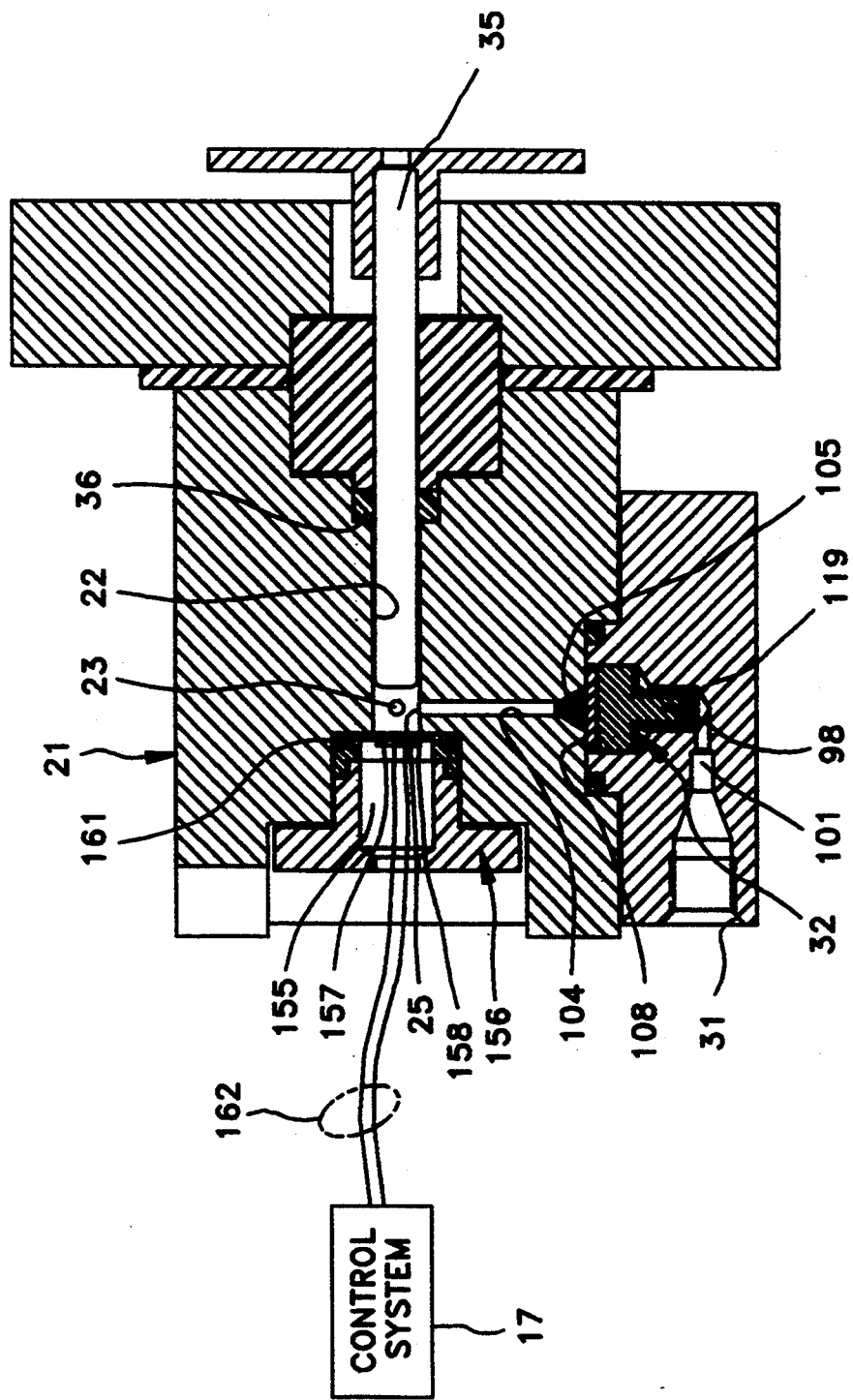
FIG. 5a is a cross sectional side view of the system shown in FIGS. 2–4.
Figure 7:
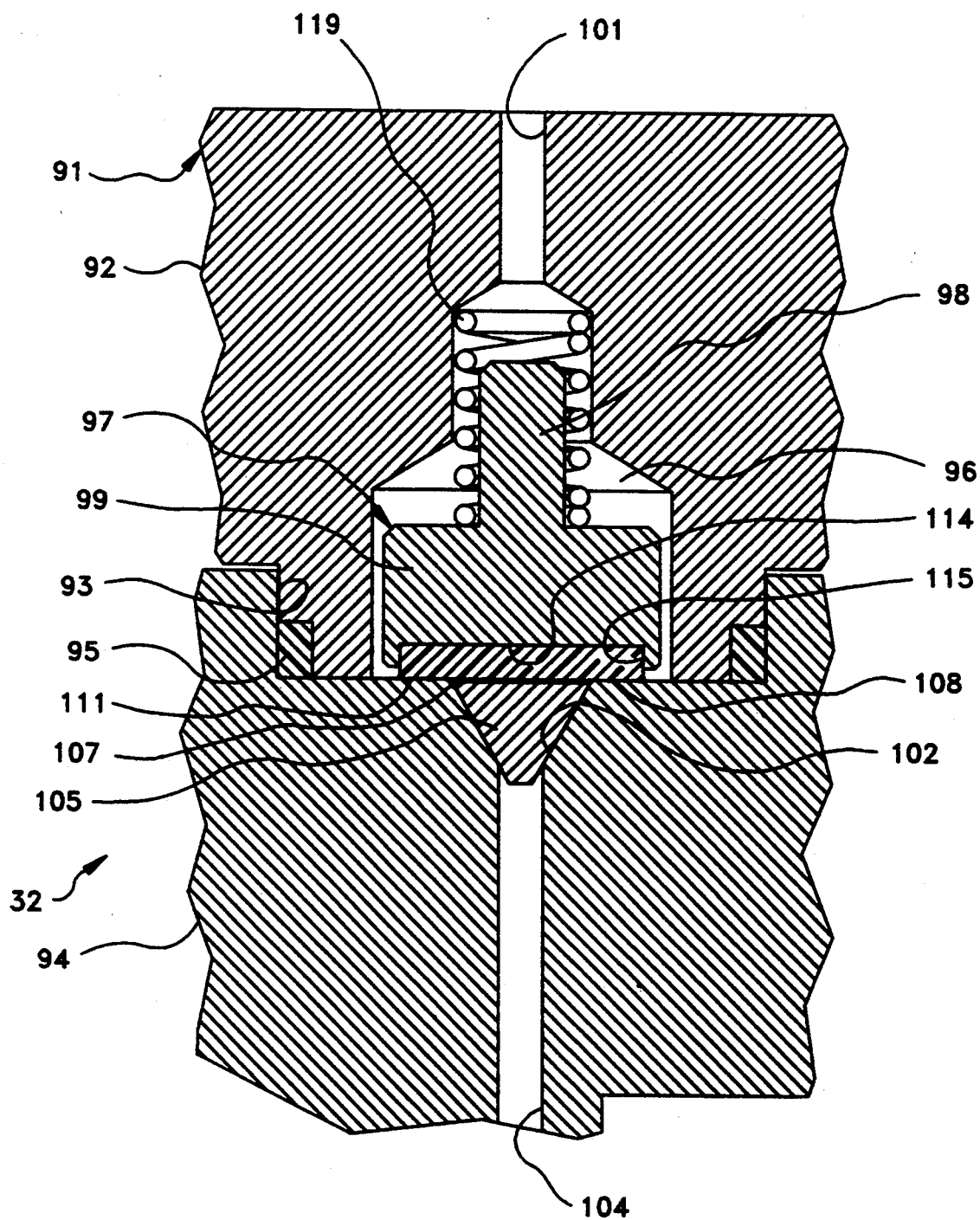
FIG. 7 is a cross sectional view of an outlet liquid valve (shown closed) of the pumping system shown in FIGS. 2–5.
Figure 8:
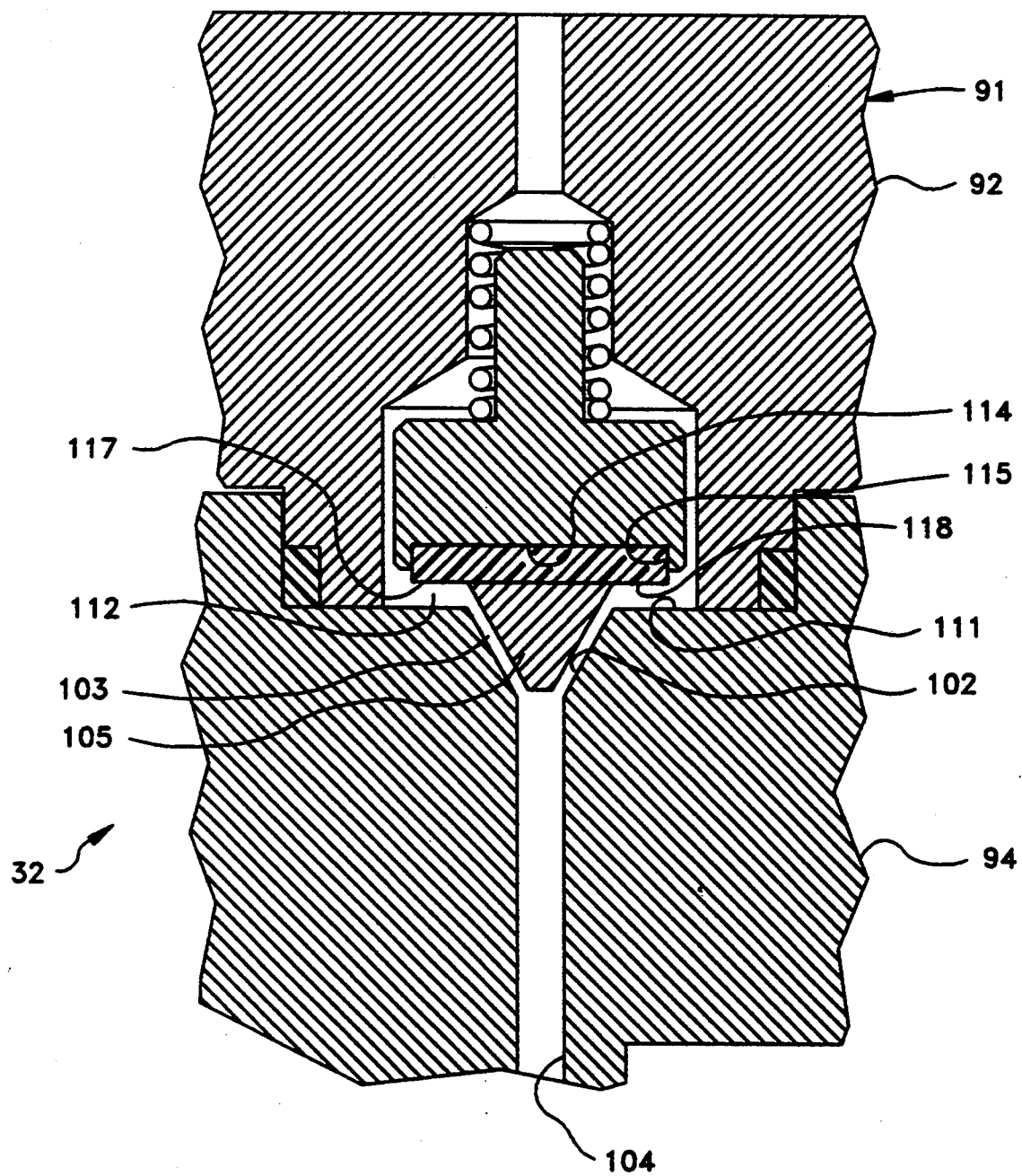
FIG. 8 is a cross sectional view of the outlet valve of FIG. 7 in an open condition.

Illustrated in FIGS. 7 and 8 is the outlet valve 32 connecting the outlet port 25 (FIG. 5a) and the outlet opening 31. A valve body 91 includes a first portion 92 received by a recess 93 in a second portion 94 and sealed therein by an annular seal 95. Retained by a cavity 96 in the first body portion 92 is an actuator 97 having a stem portion 98 and an enclosure portion 99. Extending from the cavity 96 is an outlet passage 101 communicating with the outlet opening 31 (FIG. 5a). The second valve body portion 94 defines a conically shaped first valve seat 102 forming a first passage 103. Extending out of the first passage 103 is an inlet passage 104 communicating with the outlet port 25 (FIG. 5a). A conically shaped first closure plug 105 is movable in the first passage 103 between an open position (FIG. 8) spaced from the first seat 102 so as to permit liquid flow through the first passage 103 and a closed position (FIG. 7) engaging the first seat 102 and filling the first passage 103 so as to prevent liquid flow therethrough. In its closed position, the first closure 105 engages the first seat 102 along an annular joint 107 that surrounds a planar contact surface 108 formed at an end of the plug 105.

The recess 93 in the second valve body portion 94 forms an annular planar second seat 111 surrounding the joint 107 and aligned with the planar contact surface 108 with the plug 105 in its closed position. As shown, the seat surface 111 intersects and is transverse to the first passage 103. Defined by the second seat 111 is a second passage 112 in series with the first passage 103 and communicating with the cavity 96 in the first valve body portion 92. Formed in the enclosure portion 99 of the actuator 97 is a circular recess having a planar inner surface 114 and an edge surface 115 extending perpendicular thereto. A second disc closure element 117 is retained by the recess in the enclosure portion 99 and has an exposed, planar outer surface 118. Substantially all of the disc 117 with the exception of the outer surface 118 is abutted and confined by the inner and edge engagement surfaces 114, 115 of the enclosure portion 99. The actuator portion 97 is movable between an unseated position (FIG. 8) wherein the outer surface 118 of the disc 117 is spaced from the second seat 111 so as to permit liquid flow through the second passage 112 into the cavity 96 and a seated position (FIG. 7) in which the outer surface 118 of the disc 117 engages the second seat 111 to prevent liquid flow through the second passage 112. In addition, the outer surface 118 of the disc 117 covers the annular joint 107 and engages the planar contact surface 118 on the plug 105. A coiled spring 119 surrounds the stem portion 98 of the actuator 97 and is engaged between the enclosure portion 99 thereof and the first valve body portion 92. Exerted by the spring 119 is a bias that forces the enclosure portion 99 in a direction that produces the seated position of the second disc closure 117 and the closed position of the first plug closure 105 and shown in FIG. 7.

The second valve body portion 94, the first plug closure 105 and the enclosure portion 99 of the actuator 97 are formed with materials having a given substantial hardness with a preferable material being stainless steel. Conversely, the second disc closure 117 is formed with a material having a hardness substantially less than the given hardness with a preferred material being Teflon plastic. When in its seated position (FIG. 7), the relatively soft disc 117 engages the hard second seat 111 to create a tight seal that prevents liquid flow through the first and second passages 103, 112. In addition, cold flow deterioration of the disc closure 117 is prevented by its confinement between the engaging surfaces 114, 115 of the enclosure portion 99, the second annular seat 111 and the planar contact surface 118 of the first plug closure 105. The extremely small opening existing at the annular joint 107 is insufficiently large to accommodate cold flow of the disc closure 117. However, in response to the existence of pressure at the inlet passage 104 that overcomes the bias of the spring 119, the first plug closure 105 and the second disc closure 117 are moved, respectively, to their open end unseated positions shown in FIG. 8 to establish full liquid flow between the inlet passage 104 and the outlet passage 101. Although tiny particles carried by the liquid flow through the valve 32 could prevent full closure of the plug 105 against the conical first seat 103, the extremely small opening resulting will not support cold flow of the disclosure 117. Conversely, such tiny particles trapped in the second passage 111 are merely wedged into the relatively soft disc closure 117 by the engaging annular seat 111 and contact surface 108 of the plug 105. Thus, the seated relatively soft disc closure 117 provides the valve 32 with a tight liquid seal while the relatively hard plug closure 105 prevents cold flow that would diminish the operating life of the disc closure 117.

Figure 9:
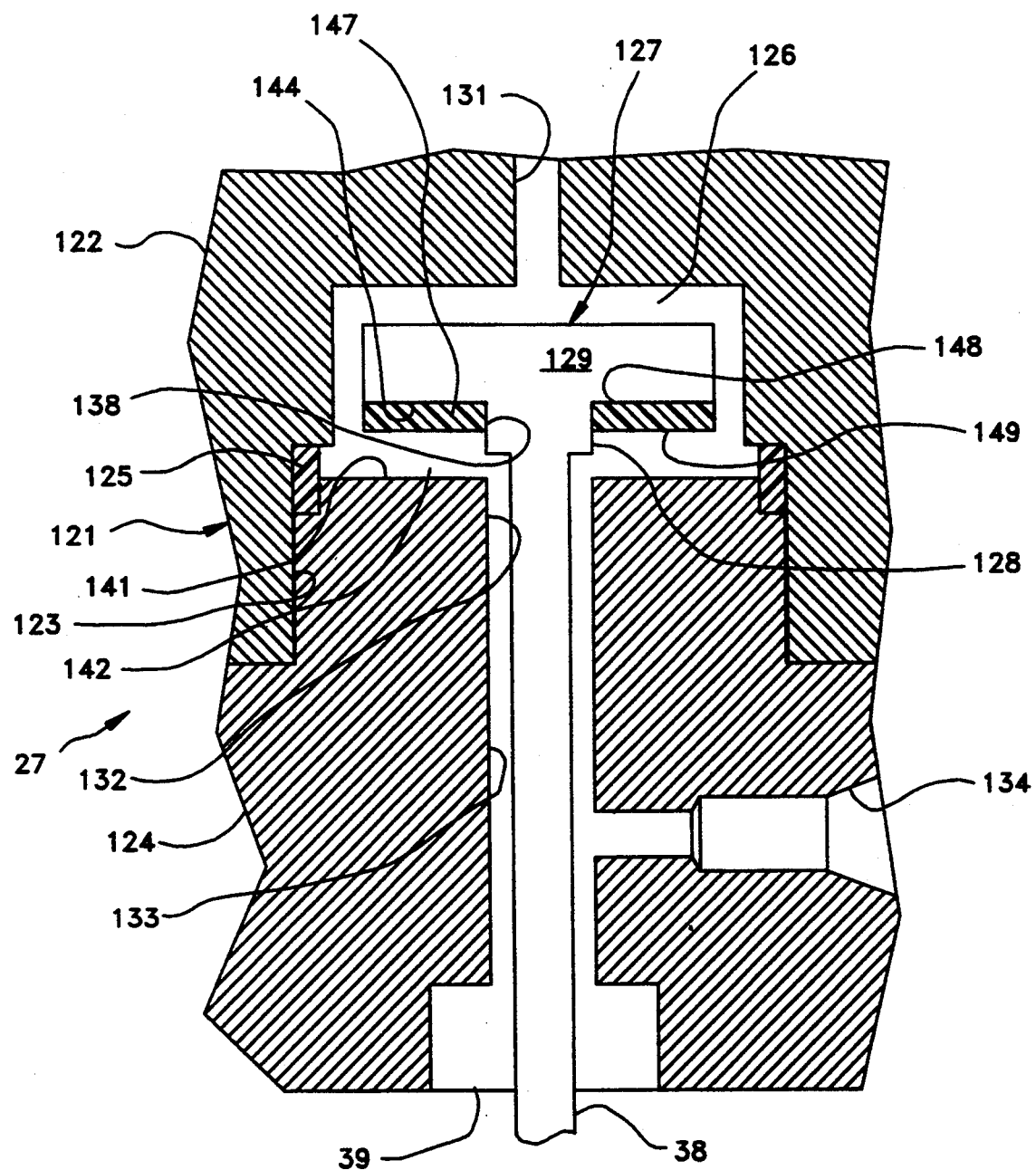
FIG. 9 is a cross sectional view of an inlet valve (shown open) of the pumping system shown in FIGS. 2–5.
Figure 10:
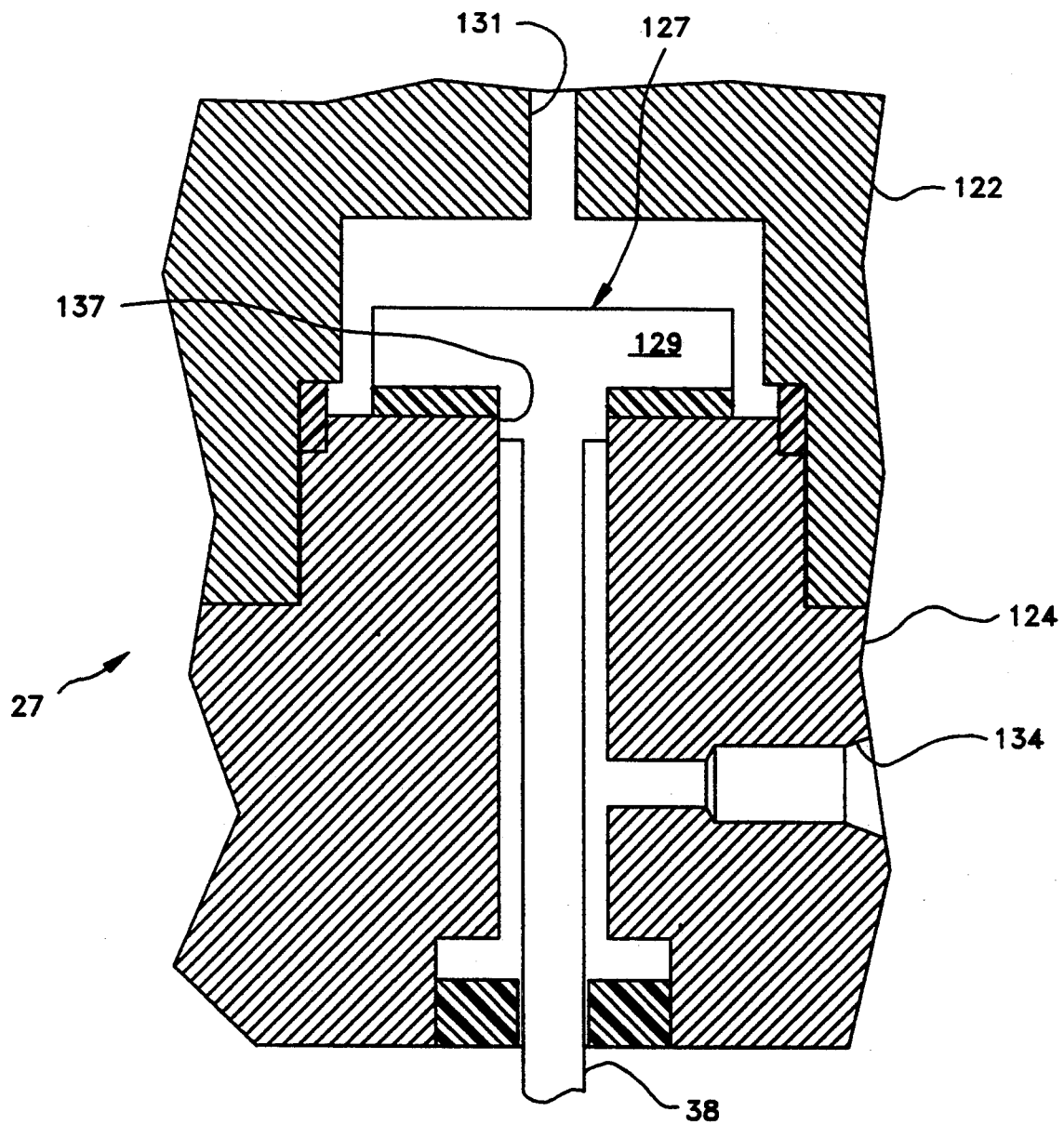
FIG. 10 is a cross sectional view of the inlet valve of FIG. 9 in a closed condition.

Illustrated more clearly in FIGS. 9 and 10 is the inlet valve 27 shown in FIG. 5. A valve body 121 includes a first portion 122 having a recess 123 and a second portion 124 received by the recess and sealed thereby by an annular seal 125. Retained by a cavity 126 in the first body portion 122 is an actuator 127 having an enclosure portion 129 and a first closure plug portion 128 joined to the inlet actuator 38. Extending from the cavity 126 is an outlet passage 131 communicating with the inlet port 23 (FIG. 5). The second valve body portion 124 defines a cylindrically shaped first valve seat 132 forming a first passage 133. Extending out of the first passage 133 is an inlet passage 134 communicating with the inlet opening 26 (FIG. 5). The inlet solenoid 37 (FIG. 5) moves the cylindrically shaped first closure plug 128 in the first passage 133 between an open position (FIG. 9) spaced from the first seat 132 so as to permit liquid flow through the first passage 133 and a closed position (FIG. 10) engaging the first seat 132 and filling the first passage 133 so as to prevent liquid flow therethrough. In its closed position, the first plug closure 128 engages the first seat 132 along an annular joint 137 and includes a cylindrical contact surface 138 portion projecting out of the first passage 133. The recess 123 in the second valve body portion 124 forms an annular planar second seat 141 surrounding one side of the joint 137 and transverse to the passage 133 and the contact surface 138 which extends from an opposite side of the joint 137. Defined by the second seat 141 is a second passage 142 in series with the first passage 133 and communicating with the cavity 126 in the first valve body portion 122. Formed by the enclosure portion 129 of the actuator 127 is an annular planar engagement surface 144 extending parallel to the second seat 141. A second annular disc closure element 147 is retained by the enclosure portion 129 and includes an inner surface 148 engaging the engagement surface 144, an outer surface 149, and an inner edge surface 151 engaging the contact surface 138 of the plug 128. Substantially all the entire outer surface of the disc 137 with the exception of the outer surface 149 is abutted and confined by the enclosure portion 129. The actuator portion 127 is movable between an unseated position (FIG. 9) wherein the outer surface 149 of the disc 137 is spaced from the second seat 141 so as to permit liquid flow through the second passage 142 into the cavity 126 and a seated position (FIG. 10) in which the outer surface 149 of the disc 137 engages the second seat 141 to prevent liquid flow through the second passage 142.

The second valve body portion 124, the first plug closure 128 and the enclosure portion 129 of the actuator 127 are formed with a material having a given substantial hardness such as stainless steel. Conversely, the second disc closure 137 is formed with a material having a hardness substantially less than the given hardness with a preferred material being Teflon plastic. When in its seated position (FIG. 10), the relatively soft disc 147 engages the hard second seat 141 to create a tight seal that prevents liquid flow through the first and second passage 133, 142. In addition, cold flow deterioration of the disc closure 147 is prevented by its confinement by the engagement surface 144 of the enclosure portion 127, the second annular seat 141 and the cylindrical contact surface 138 of the first plug closure 128. Thus, the seated relatively soft disc closure 147 provides the inlet valve 27 with a tight liquid seal while the relatively hard plug closure 128 prevents cold flow that would diminish the operating life of the disc closure 147. The purge valve 34 (FIG. 5) is identical to the inlet valve 27 and is controlled in the same manner by the purge solenoid 41.

Referring again to FIG. 5, the pump head assembly 21 defines a cavity 155 that communicates with the pump chamber 22 adjacent to the outlet port 25. Retained by the cavity 155 is a pressure transducer assembly 156 that includes a strain gage 157 mounted on a flexible diaphragm 158. The transducer assembly 156 is pressure sealed in the cavity 155 by an annular seal 161. Monitored by the transducer 156 is the fluid pressure in the pump chamber 22 and signals indicative thereof are fed by lines 162 to the computer control system 17.

Figure 2:
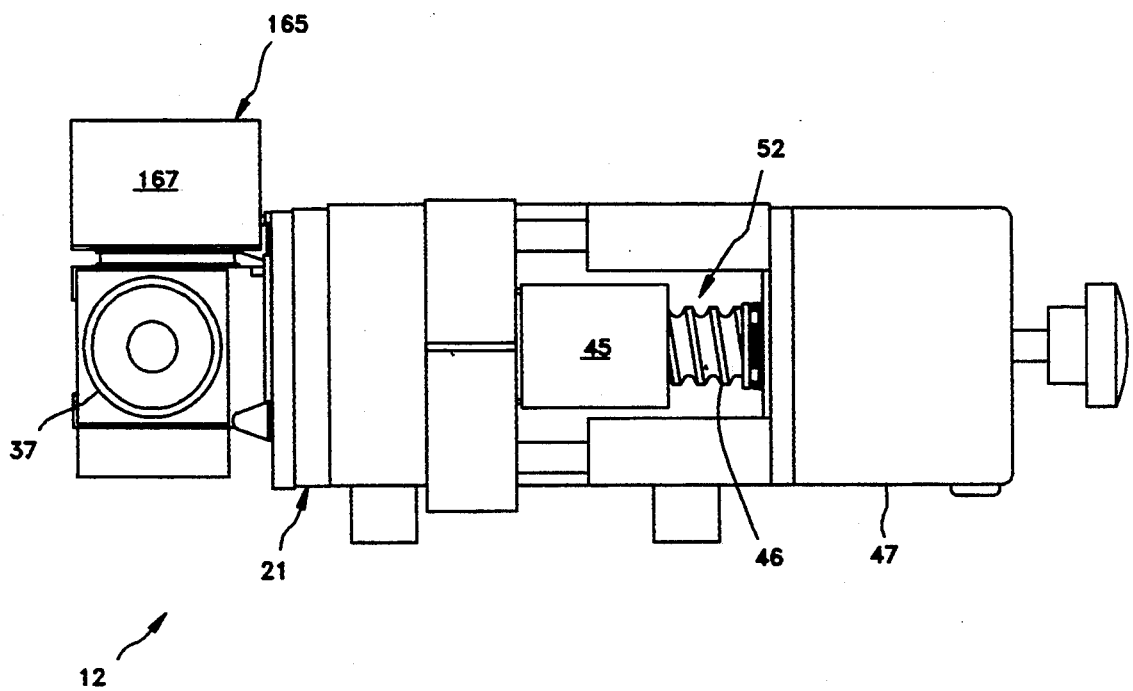
FIG. 2 is a side elevational view of the pumping system shown in FIG. 1.

As shown in FIGS. 2-4, a cooling assembly 165 is mounted on the pump head assembly 21 directly above the pump chamber 22. Included in the cooling assembly 165 is a thermo electric cooling unit 166 mounted directly on that portion of the head assembly 21 defining the pump chamber 22. Disposed directly above and in thermal contact with the thermo electric cooling unit 26 is a heat sink formed by a plurality of heat conducting fins 167. The cooling assembly 165 compensates for heat produced by the inlet and purge solenoids 37, 41 and for ambient heat in the surrounding environment to maintain that portion of the head assembly 21 defining the pump chamber 22 at a constant temperature. Preferably, the constant temperature is slightly below the lowest expected ambient temperature in the room housing the pumping system 12. By providing a constant relatively cool temperature for the head assembly 21, problems associated with the formation of gas bubbles and density changes in the mobile phase are reduced.

OPERATION

During operation of the liquid chromatography apparatus 11, the pumping system 12 during a backward stroke of the plunger 35 draws liquid from the mobile phase source 13 through the inlet valve 27 (FIG. 5) into the pumping chamber 22. A subsequent forward stroke of the plunger 35 discharges liquid through the outlet port 25 and the outlet valve 32 (FIGS. 7 and 8) for injection into the separation column 15. During this operation of the pumping system 12, the sensor assembly 156 monitors the pressure in the pump chamber 22. In response to the pressure information provided by the sensor assembly 156, the computer control system 17 controls the inlet solenoid 37, the purge solenoid 41 and the electric motor 47 to establish desired operation of the head assembly 21. For example, during a backstroke of the piston plunger 35, the inlet valve 27 is maintained in a closed condition until the pressure in the pump chamber 22 is reduced to the pressure at the inlet opening 26, typically atmospheric. At that time, the inlet solenoid 37 opens the inlet valve 27 causing the remaining backstroke of the plunger 35 to draw liquid into the pump chamber 22. Consequently, problems such as liquid degassing and liquid surges associated with pumping chamber vacuums created by pumps employing inlet check valves are eliminated. Similarly eliminated are problems commonly produced by timed cam operated inlet valves that open near the end of a forward plunger stroke. Such operation can prompt reverse liquid flow through the inlet valve to produce agitation therein and an undefined amount of liquid flow.

Other problems eliminated by the pumping system 12 are those associated with the inadvertent presence of air bubbles in the pump chamber 22. The pressure sensor 156 and control system 17 monitor the displacement of the plunger 35 during the initial portion of a forward stroke until a dramatic pressure increase is detected and that displacement is dependent on the volume of air present in the pumping chamber 22. Such trapped air adversely affects the performance of a pump and is not easily discharged through the spring loaded outlet valve 32. When the control system 17 has determined that an excessive amount of air is trapped in the pump chamber 22, the purge valve 34 is opened by the purge solenoid 41 during a forward stroke of the piston plunger 35. Since the purge opening 33 (FIG. 5) is at atmospheric pressure, the forward stroke of the piston 35 discharges substantially all of the liquid and trapped air in the pump chamber 22 through the purge valve 34. After adequate purging of the trapped air, the control system 17 causes the purge solenoid 41 to close the purge valve 34 and allowing the head assembly 21 to resume normal operation.

The pressure sensor 156 and computer control system 17 also can provide other types of information useful in controlling the head assembly 21 so as to provide therewith desired performance such as a constant volume flow rate or a constant mass flow rate. For example, during a given cycle of the pump 21, the plunger 35 can be stopped in a mid-portion of its forward stroke after which the pressure in the pumping chamber 22 is monitored. A decrease in pressure within the pumping chamber 22 will indicate leaks through the liquid seals or through the inlet valve 27. Conversely, a rise of pressure in the pump chamber 22 will indicate back leakage through the outlet valve 32 from the high pressure portion of the system. The information derived by the pressure sensor 156 can be used by the control system 17 to induce corrective adjustments in pump operation or to determine the existence of a pump dysfunctional for particular requirements.

OTHER EMBODIMENTS

Figure 11:
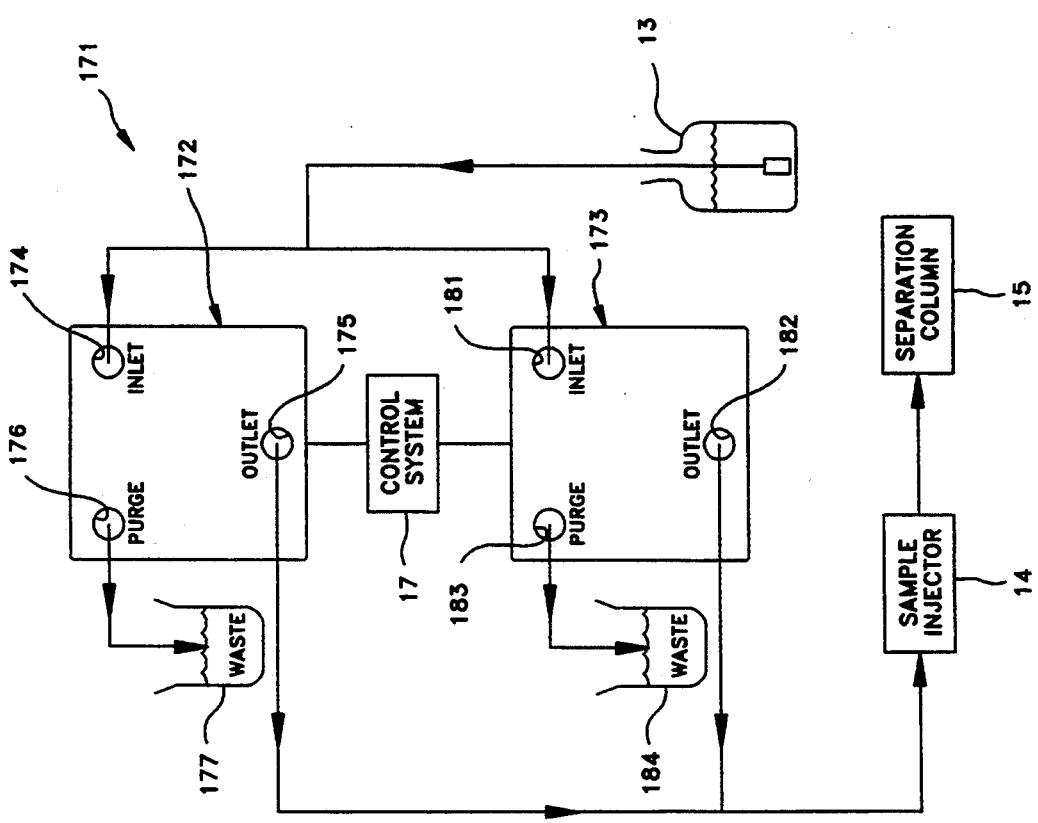
FIG. 11 is a block diagram illustrating another pumping system embodiment.

FIG. 11 illustrates another embodiment 171 including a first pump 172 and a second pump 173, each identical to the pump head 21 described above. The first pump 172 has a first inlet 174 connected to the mobile phase source 13, a first outlet 175 connected to the separation column 15 and a purge opening 176 connected to an atmospheric waste reservoir 177. Similarly, the second pump 173 has a second inlet 181 connected to the mobile phase source 13 an outlet 182 connected to the separation column 15 and a purge opening 183 connected to an atmospheric waste reservoir 184. The first and second pumps 172, 173 are operated in sequence by the control system 17 such that when the first pump 172 is filling, the second pump 173 is discharging and vice versa. By utilizing the information provided by the pressure sensors 156, the control system 17 operates the first and second pumps 172, 173 so as to provide a highly constant and predictable liquid flow to the column 15. Preferably, the control system 17 starts a forward stroke of the second pump 173 so as to provide in its pumping chamber, at the completion of a forward stroke by the first pump 172, a pressure equal to the system pressure at the outlets 175, 192 and initiates a forward stroke of the first pump 172 so as to produce in its pumping chamber, at the completion of a forward stroke by the second pump 173, a pressure equal to that system pressure. Thus, the flow to the separation column 15 is highly constant without a requirement for damping.

In response to detection by the pressure sensors 156 of pumping deterioration in either of the pumps 172 or 173 in the manner described above, the control system 17 can correct the deterioration by adjusting operation of the deficient pump or can induce complementary compensating adjustment in the operation of the alternate pump. Such adjustments can include, for example, changes in either the lengths or speed of the pump plungers forward and backward strokes. In the event that the control system 17 detects an intolerable level of trapped air in either of the pumps 172, 173, its purge valve 34 can be opened to provide a purging discharge through one of the purge openings 176 or 183. Preferably, an alternate pump would be stopped during purging of a contaminated pump and subsequently the speeds of both pumps would be increased to restore a desired average flow rate from the parallel combination. It will be noted that the corrective operations described above for the embodiment 171 required that each of the first and second pumps 172, 173 be provided with independently operated drive motors and operating solenoids.

Figure 12:
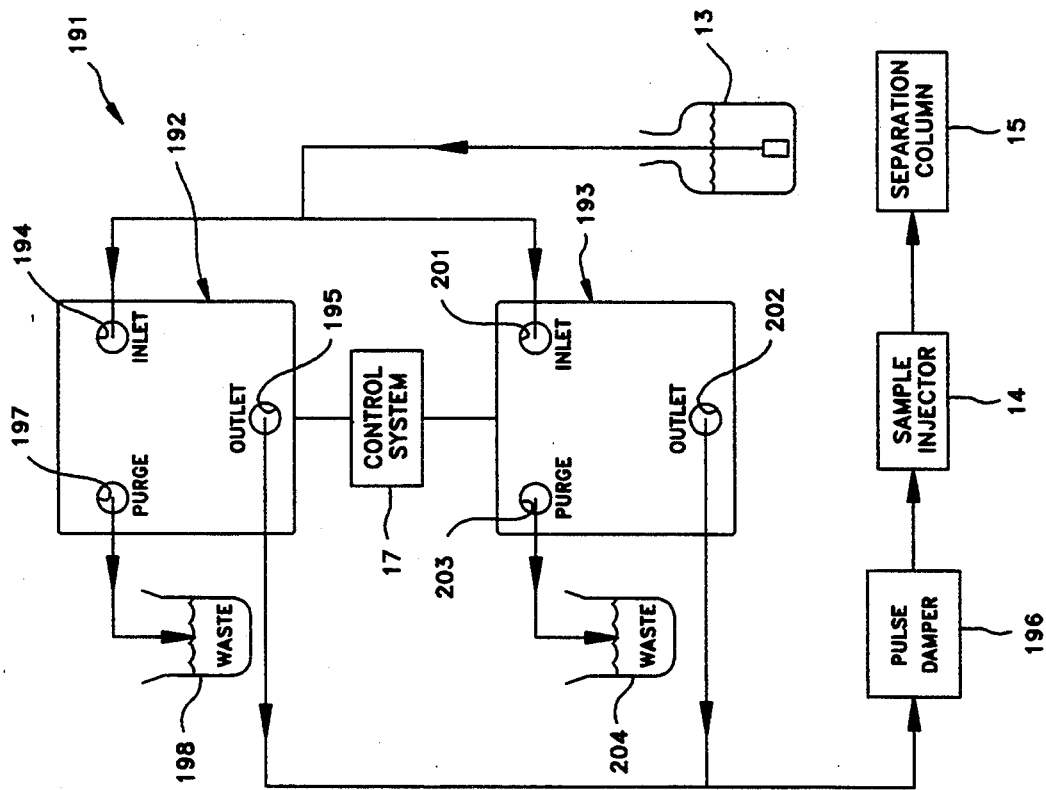
FIG. 12 is a block diagram illustrating an additional pumping system embodiment.

FIG. 12 illustrates another embodiment 191 including a primary pump 192 and an auxiliary pump 193 each identical to the pump head assembly 21. The primary pump 192 includes a primary inlet opening 194 connected to the mobile phase source 13, a primary outlet opening 195 connected to the separation column 15 by a pulse damper 196 and a primary purge opening 197 connected to an atmospheric waste reservoir 198. Similarly, the auxiliary pump 193 includes an auxiliary inlet opening 201 connected to the mobile phase source 13, an auxiliary outlet opening 202 connected to the pulse damper 196 and an auxiliary purge opening 203 connected to an atmospheric waste reservoir 204.

During normal operation of embodiment 191, the primary pump 192 functions in the manner described above for the pump head assembly 21 to produce a flow of liquid from the mobile phase source 13 to the separation column 15. Assuming normal operation of the primary pump 192, the auxiliary pump 193 remains on a standby, inactive status. However, in response to the detection by the pressure sensor 156 and control system 17 of an intolerable deterioration in the mass flow rate pumping performance of the primary pump 192, the control system 17 functions to deactivate the primary pump 192, the control system 17 functions to deactivate the primary pump 192 and activate the auxiliary pump 193 thus maintaining the flow of liquid between the mobile phase source 13 and the separation column 15. Again, the described operation of the embodiment 191 requires that each of the primary and auxiliary pumps 192, 193 is equipped with its own operating motor and solenoid valves.

Figure 13:
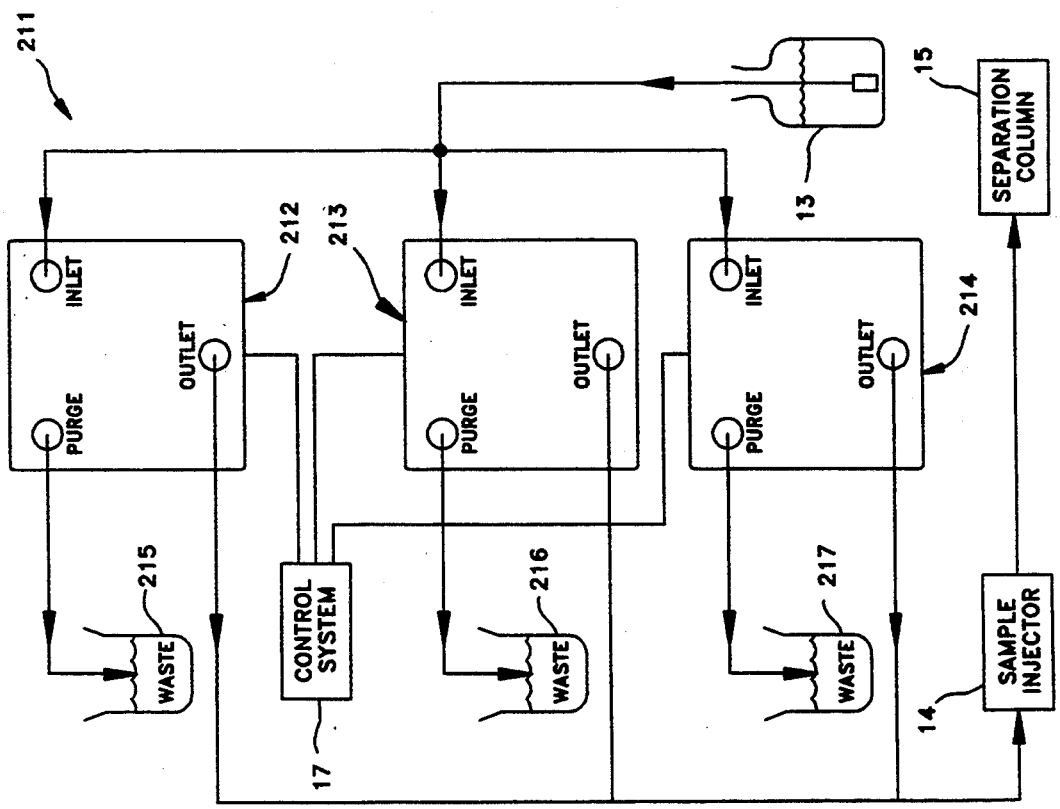
FIG. 13 is a block diagram illustrating a pumping system embodiment including a reserve pump.

Illustrated in FIG. 13 is another embodiment 211 including a pair of primary pumps 212, 213 and an auxiliary pump 214. Each of the pumps 212–214 is identical to the pump head assembly 21 and has an inlet connected to the mobile phase source 13 and an outlet connected to the separation column 15. In addition, each pump 212–214 has a purge opening connected to a waste reservoir 215–217, respectively. During normal operation the embodiment 211, the primary pumps 212, 213 function in tandem in the same manner as embodiment 171 described above to provide a constant flow to the separation column 15. However, in response to detection by the pressure sensor 156 of an intolerable deterioration in the pumping performance of either of the primary pumps 212, 213, the control system 17 will deactivate the dysfunctional pump and activate the auxiliary pump 214 to maintain uninterrupted constant flow to the separation column 15.

Figure 14:
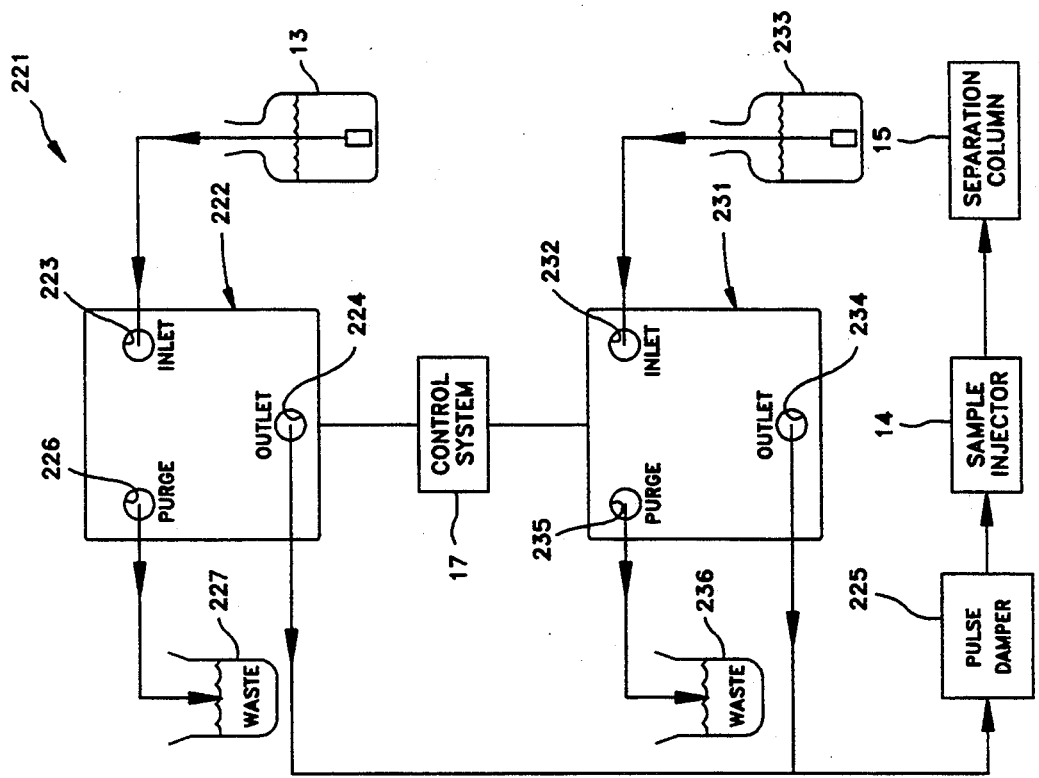
FIG. 14 is a block diagram illustrating a gradient type pumping system embodiment.

FIG. 14 illustrates another embodiment 221 including a first pump 222 having an inlet opening 223 connected to the mobile phase source 13, an outlet 224 connected to the separation column 15 by a pulse damper 225 and a purge opening 226 connected to a waste reservoir 227.

Also included in the embodiment 221 is a second pump 231 having an inlet opening 232 connected to a different mobile phase supply 233, an outlet opening 234 connected to the pulse damper 225 and a purge opening 235 connected to a waste reservoir 236. Each of the first and second pumps 222, 231 is identical to the pump head assembly 21. During normal operation, the pumps 222 and 223 function as described above to draw mobile phase from the different sources 13, 233 and provide a gradient flow to the separation column 15. Preferably, the first and second pumps are controlled such that both pumps deliver at the time their contribution to the gradient flow and refill simultaneously. In response to deterioration in pumping performance detected by a pressure sensor 156 in either pump, the control system 17 would introduce corrective measures as described above.

Figure 15:
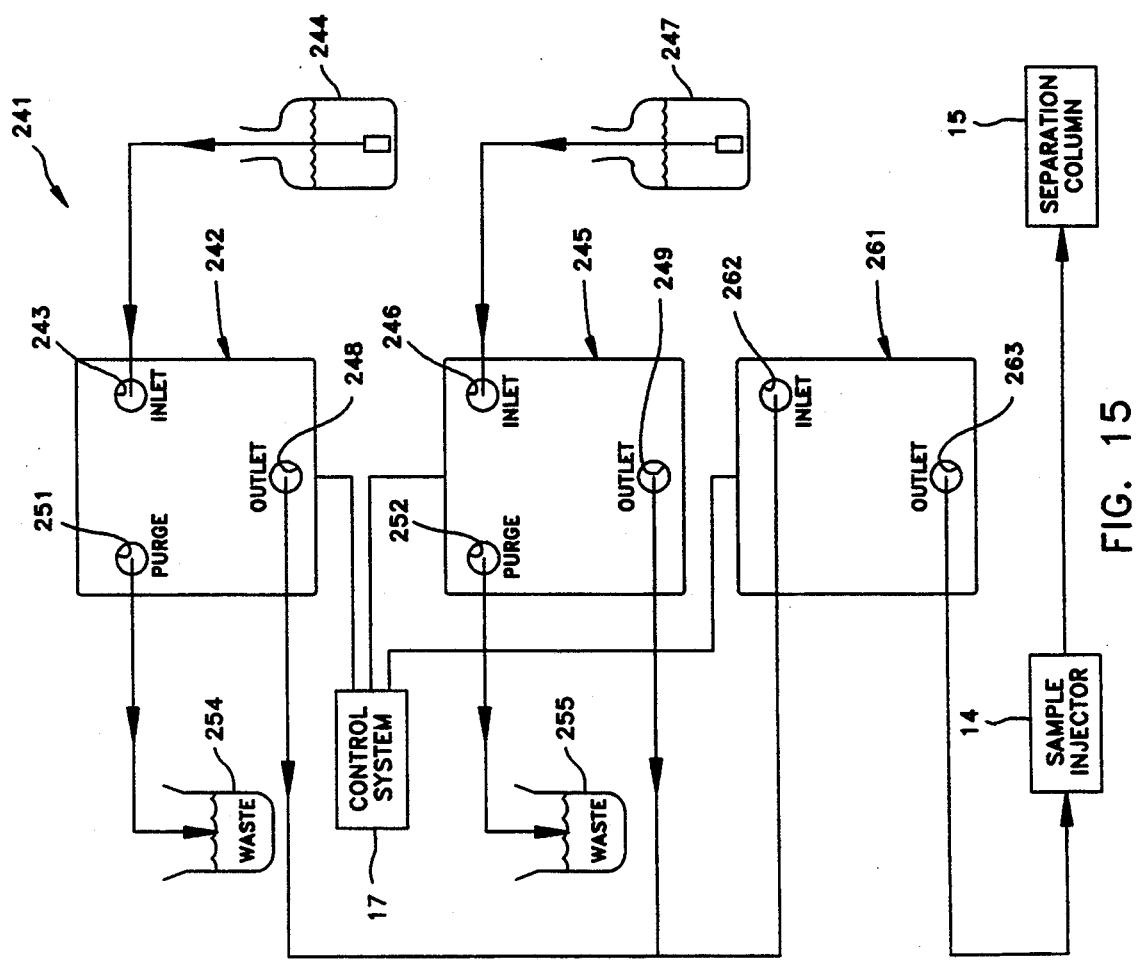
FIG. 15 is a block diagram illustrating a pumping system embodiment with an active damper pump.

FIG. 15 illustrates another embodiment 241 having a first pump 242 with an inlet opening 243 connected to a source 244 of mobile phase and a second pump 245 having an inlet opening 246 connected to a supply 247 of mobile phase. Each of the first and second pumps 242 and 245 is identical to the pump head assembly 21 and their outlet openings 248 and 249, respectively, are interconnected. Purge openings 251, 252 of the pumps 242 and 245 are connected to waste reservoirs 254 and 255, respectively. Also included in the embodiment 241 is a third or damper pump 261 having an inlet opening 262 connected to the outlet openings 248 and 249 of the first and second pumps 242, 245. An outlet opening 263 of the damper pump 261 is connected to the separation column 15 while a purge opening 264 is connected to a waste reservoir 265. The damper pump 261 also is identical to the pump head assembly 21 except for the elimination of the inlet valve 27, the inlet solenoid 37, the purge valve 34, the purge solenoid 41 and the outlet valve 32.

During normal operation of the embodiment 241, the control system 117 drives the first and second pumps 242 and 245 to provide a gradient flow to the inlet opening 262 of the damper pump 261. Because of their synchronized operation, the first and second pumps 242, 245 provide at their inter-connected outlets a uniform mobile phase composition. The damper pump 261 is operated by the control system 17 out of synchronism with the pumps 242, 245 so as to take in flow during a portion of their pumping strokes and then produce flow from its outlet 263 during a portion of their backstrokes. Since the composition delivered to it's inlet 262 is modified in the damper pump 261 during its backstroke, the control system 17 minimizes the time required for that backstroke. Thus, modification in the gradient composition delivered by the damper pump 261 also is minimized. This operation is made possible by the provision of a damper pump 261 with an independently controlled motor.

Obviously, many modifications and variations of the present invention are possible in light of the above teachings. It is to be understood, therefore, that the invention can be practiced otherwise than as specifically described.

What is claimed is:
1. Machine apparatus comprising:
a drive shaft adapted for reciprocating motion on an axis;
an actuator shaft mounted for reciprocating rectilinear motion on said axis; and coupling means coupling one end of said drive shaft to one end of said actuator shaft so as to transmit said reciprocating motion of said drive shaft to said actuator shaft; said coupling means comprising a pivot joint for allowing relative pivotal movement between said drive shaft and said actuator shaft, and a translational joint for allowing relative translational movement between said one end of said drive shaft and said one end of said actuator shaft in directions transverse to said axis and wherein said translational joint comprises a flexible means connecting said pivot joint and said one end of said drive shaft.

2. A machine apparatus according to claim 1 wherein said pivot joint is fixed to said one end of said actuator shaft, and said translational joint is connected to said one end of said drive shaft.

3. A machine apparatus according to claim 2 wherein said pivot joint is a ball and socket joint, and said translational joint comprises an annular ball bearing assembly disposed concentrically with said axis and engaged between a planar surface portion of said socket joint and a planar surface on said one end of said drive shaft.

4. A machine apparatus according to claim 3 wherein said flexible means is a flexible member extending through a central opening in said annular ball bearing assembly and having ends secured, respectively, to said socket joint and said one end of said drive shaft.

5. A machine apparatus according to claim 1 wherein said coupling means further comprises a fastener means allowing separation of said drive shaft and said actuator shaft in response to a single step of applying therebetween opposing forces aligned with said axis.

6. A machine apparatus according to claim 5 wherein said fastener means comprises a permanent magnet.

7. A machine apparatus according to claim 5 wherein said pivot joint is fixed to said one end of said actuator shaft, and said translational joint is connected to said one end of said drive shaft.

8. A machine apparatus according to claim 7 wherein said pivot joint is a ball and socket joint, and said translational joint comprises an annular ball bearing assembly disposed concentrically with said axis and engaged between a planar surface portion of said socket joint and a planar surface on said one end of said drive shaft.

9. A machine apparatus according to claim 1 including a hydraulic cylinder, and wherein said actuator shaft includes a piston portion mounted within said cylinder for reciprocating movement relative thereto.

10. A machine apparatus according to claim 9 wherein said pivot joint is fixed to said one end of said actuator shaft, and said translational joint is connected to said one end of said drive shaft.

11. A machine apparatus according to claim 10 wherein said pivot joint is a ball and socket joint, and said translational joint comprises an annular ball bearing assembly disposed concentrically with said axis and engaged between a planar surface portion of said socket joint and a planar surface on said one end of said drive shaft.

12. A machine apparatus according to claim 11 wherein said flexible means is a flexible member extending through a central opening in said annular ball bearing assembly and having ends secured, respectively, to said socket joint and said one end of said drive shaft.

13. A machine apparatus according to claim 9 wherein said hydraulic cylinder is a pump chamber of a liquid chromatography pumping system.

14. Machine apparatus comprising:
a drive shaft adapted for reciprocating motion on an axis;
an actuator shaft mounted for reciprocating rectilinear motion on said axis; and
coupling means coupling one end of said drive shaft to one end of said actuator shaft so as to transmit said reciprocating motion of said drive shaft to said actuator shaft; said coupling means comprising a pivot joint for allowing relative pivotal movement between said drive shaft and said actuator shaft, a translational joint for allowing relative translational movement between said one end of said drive shaft and said one end of said actuator shaft in directions transverse to said axis, said pivot joint and said translational joint being connected in series between said one end of said actuator shaft and said one end of said drive shaft, and fastener means allowing separation of said drive shaft and said actuator shaft in response to a single step of applying therebetween opposing forces aligned with said axis.

15. A machine apparatus according to claim 14 wherein said pivot joint is fixed to said one end of said actuator shaft, and said translational joint is connected to said one end of said drive shaft.

16. A machine apparatus according to claim 15 wherein said pivot joint is a ball and socket joint, and said translational joint comprises an annular ball bearing assembly disposed concentrically with said axis and engaged between a planar surface portion of said socket joint and a planar surface on said one end of said drive shaft.

17. A machine apparatus according to claim 14 wherein said fastener means comprises a permanent magnet.

18. A machine apparatus according to claim 14 including a hydraulic cylinder, and wherein said actuator shaft includes a piston portion mounted within said cylinder for reciprocating movement relative thereto.

19. A machine apparatus according to claim 18 wherein said hydraulic cylinder is a pump chamber of a liquid chromatography pumping system.

20. A machine apparatus according to claim 19 wherein said fastener means comprises a permanent magnet.

* * * * *